US011363424B2

(12) United States Patent
Ting et al.

(10) Patent No.: US 11,363,424 B2
(45) Date of Patent: *Jun. 14, 2022

(54) LOCATION-BASED RESOURCE MANAGEMENT

(71) Applicants: David Ting, Sudbury, MA (US); Gus Malezis, Stouffville (CA); Jason Mafera, Francestown, NH (US); Alain Slak, Bedford, MA (US); Aaron Miri, Natick, MA (US); Paul Oramasionwu, Somerville, MA (US)

(72) Inventors: David Ting, Sudbury, MA (US); Gus Malezis, Stouffville (CA); Jason Mafera, Francestown, NH (US); Alain Slak, Bedford, MA (US); Aaron Miri, Natick, MA (US); Paul Oramasionwu, Somerville, MA (US)

(73) Assignee: IMPRIVATA, INC., Lexington, MA (US)

( * ) Notice: Subject to any disclaimer, the term of this patent is extended or adjusted under 35 U.S.C. 154(b) by 557 days.

This patent is subject to a terminal disclaimer.

(21) Appl. No.: 15/843,460

(22) Filed: Dec. 15, 2017

(65) Prior Publication Data

US 2018/0109936 A1 Apr. 19, 2018

Related U.S. Application Data

(63) Continuation-in-part of application No. 14/945,658, filed on Nov. 19, 2015.

(Continued)

(51) Int. Cl.
*G06F 15/16* (2006.01)
*H04W 4/30* (2018.01)
*H04W 12/06* (2021.01)
*H04W 4/029* (2018.01)
*G16H 10/60* (2018.01)
*H04W 4/021* (2018.01)

(Continued)

(52) U.S. Cl.
CPC .............. *H04W 4/30* (2018.02); *G16H 10/60* (2018.01); *H04W 4/029* (2018.02); *H04W 12/06* (2013.01); *H04W 4/021* (2013.01); *H04W 4/50* (2018.02); *H04W 12/63* (2021.01)

(58) Field of Classification Search
None
See application file for complete search history.

(56) References Cited

U.S. PATENT DOCUMENTS

| 8,141,075 B1* | 3/2012 | Chawla | G06F 9/45558 718/1 |
| 8,943,580 B2* | 1/2015 | Fadell | G06F 21/316 726/19 |
| 9,405,602 B1* | 8/2016 | Verne | G06F 9/545 |

(Continued)

*Primary Examiner* — Umar Cheema
*Assistant Examiner* — Gregory P Tolchinsky
(74) *Attorney, Agent, or Firm* — Morgan, Lewis & Bockius LLP (57) ABSTRACT

In various embodiments, the predicted location of a user within an institutional space is associated with a node at or near that location, and a virtual desktop is prepared before a user has actually logged on and authenticated. Although users are not accorded access to applications and sensitive data until they have properly authenticated themselves, the virtual desktop and associated data are assembled and retrieved in the background in order to eliminate delay following log-on.

30 Claims, 3 Drawing Sheets

Related U.S. Application Data (60) Provisional application No. 62/183,793, filed on Jun. 24, 2015, provisional application No. 62/081,820, filed on Nov. 19, 2014.

(51) Int. Cl.
*H04W 4/50* (2018.01)
*H04W 12/63* (2021.01)

(56) References Cited

U.S. PATENT DOCUMENTS

| | | | |
|---|---|---|---|
| 2008/0184355 A1* | 7/2008 | Walrath | G06F 11/0709 726/9 |
| 2009/0303329 A1* | 12/2009 | Morisaki | H04N 7/183 348/159 |
| 2011/0153854 A1* | 6/2011 | Chickering | H04L 63/0815 709/229 |
| 2012/0023223 A1* | 1/2012 | Branch | G06F 9/4856 709/224 |
| 2012/0144452 A1* | 6/2012 | Dyor | H04L 63/0884 726/4 |
| 2012/0233314 A1* | 9/2012 | Jakobsson | G06Q 30/0225 709/224 |
| 2013/0110537 A1* | 5/2013 | Smith | G06Q 10/06 705/2 |
| 2013/0326510 A1* | 12/2013 | Adekile | G06F 11/0709 718/1 |
| 2014/0109174 A1* | 4/2014 | Barton | H04W 12/08 726/1 |
| 2014/0122730 A1* | 5/2014 | Burch | H04L 67/146 709/228 |
| 2014/0200036 A1* | 7/2014 | Egner | H04W 8/245 455/456.3 |
| 2015/0156081 A1* | 6/2015 | Chakra | H04L 41/5006 709/224 |
| 2015/0207683 A1* | 7/2015 | Adogla | H04L 41/0893 709/223 |
| 2016/0043968 A1* | 2/2016 | Jacob | H04L 47/808 709/226 |

\* cited by examiner

LOCATION-BASED RESOURCE MANAGEMENT

RELATED APPLICATION

This is a continuation-in-part of U.S. Ser. No. 14/945,658, filed on Nov. 19, 2015, which claims priority to U.S. Provisional Application Nos. 62/081,820, filed Nov. 19, 2014, and 62/183,793, filed Jun. 24, 2015. The entire disclosures of the foregoing priority documents are hereby incorporated herein by reference.

TECHNICAL FIELD

The invention relates generally to healthcare information technology, and in particular to systems and methods for location-based management of application functionality, data, access control, and clinical collaboration.

BACKGROUND

In a busy healthcare environment, such as a hospital, clinicians roam frequently among patients, floors and buildings. Each time a clinician reaches a new location, she may require access to patient information or other medical data maintained by the facility (or elsewhere). That data may be accessed via a local, typically shared workstation, or via a handheld wireless device, such as a "smart phone" or tablet capable of hosting applications and establishing telecommunications, Internet and/or local intranet connections.

In particular, medical institutions from hospitals to physician practice groups to testing centers maintain diverse electronic medical records (EMR) systems, which collectively form the healthcare information backbone. EMR systems allow clinicians access to medical information maintained in various back-end systems. The typical workflow when a physician interacts with a patient involves first logging onto the computer system, then launching and logging into one or more EMR applications, selecting the right patient record, verifying that the record matches the patient, reviewing results (often from different sources), checking up on medical references, entering orders or prescriptions (e.g., using computerized physician order entry (CPOE) applications and ePrescribing), and/or charting patient progress. All of these activities may involve the same patient but different applications, and in some cases multiple separate applications for a single patient-specific activity.

Moreover, healthcare records are protected by strict privacy laws (such as the Health Insurance Portability and Accountability Act, or HIPAA), regulatory regimes, and institutional access policies. Accordingly, when a clinician moves from place to place, he may be required to log on to a new terminal or device, and because of data-access restrictions, the log-on procedure may involve cumbersome and/or multiple authentication modalities. At the same time, an institution's security policy may also be location-dependent; for example, authentication requirements may be relaxed in controlled-access areas where occupants have already authenticated themselves.

Thus, in a healthcare environment, where people move about frequently, a busy clinician may face delays as she moves from node to node. Even if the log-on procedure is automated and the clinician need not re-authenticate, restoring a previous session—i.e., re-launching applications, querying databases for previously requested patient data, etc.— can be time-consuming. Indeed, stringent security requirements may require re-authentication using a stronger modality even at the same node. For example, a properly authenticated user may need to re-authenticate when issuing an electronic prescription for a controlled substance, and to satisfy regulatory requirements that re-authentication may involve a "strong" modality such as a fingerprint or vein scan. At the same time, clinicians may waste time re-authenticating unnecessarily following a previously successful log-in.

SUMMARY

Embodiments of the invention provide a platform for real-time location-based workflow processing. Locational events are registered and communicated to a system node (e.g., a location server) that collects and responds to event notifications as they are received. In particular, distributed applications can "subscribe" to events relevant to their operation, and when an event notification is received by the location server, it is communicated to all applications subscribing thereto—i.e., to the particular event or to an event category to which it belongs. The user's instantaneous location may be established based on the location of a currently stationary but movable device or by direct tracking, e.g., using "real-time location services" (RTLS).

Most simply, a "walkaway" event may result from a user exiting a monitored geospatial zone or entering another one. An authentication server may subscribe to events involving geospatial zones that require credentials for entry. When a clinician attempts to access a secure resource—e.g., by logging in at a workstation—the resource may consult an authentication server to determine the credentials necessary for access, since these may differ for different user groups. In addition, the required credentials may have a locational component; for example, a clinician may already have authenticated using one factor (e.g., gaining entry to a secure area using an access card), in which case only one additional factor (e.g., a password) is necessary for access to the resource. Therefore, the authentication server may subscribe to all events relevant to the security policy it implements.

The system may also support presumptive workflows, optimistic caching, and anticipatory provisioning. For example, a desktop or application server may implement optimistic caching of application data based on expected clinician movement within the institutional space, making the data available on a workstation or other device before the clinician actually reaches it. Alternatively or in addition, desktop server may implement anticipatory provisioning by storing a user's current "session" for subsequent re-creation when a clinician leaves a node or logs off the current session. In practice, this means that data sufficiently descriptive of the current user state is maintained to ease subsequent provisioning of the session on a different device. The degree of provisioning can range from re-launch of applications in use during the previous session to full re-creation of the session state prior to departure from the device or log-off, including retrieval of the data (e.g., the particular patient records or lab results being viewed in an EMR application).

As used herein, the term "session" refers broadly to the state of an application active on a user's device. Although a session may be viewed as involving both remotely hosted and purely local applications, the present invention is primarily concerned with the former—i.e., applications that may be remotely "provisioned" to the user via a virtual desktop. At the same time, it should be understood that some local applications can be replicated by remote hosting; that is, so long as an application is amenable to subsequent remote provisioning, it is immaterial for purposes of defining a "session" whether the application is currently being run locally (offline) or on a hosted basis.

Accordingly, in a first aspect, the invention relates to a method of anticipatory provisioning of resources for a mobile user in an institutional space. In various embodiments, the method comprises the steps of providing a database storing records for a plurality of users, each of the records specifying information about one of the users; acquiring a current location of a user having a record in the database; based on the acquired location and the information about the user in the corresponding database record, predicting (i) a future location of the user and (ii) stored data required by the user at the future location; causing a device at the predicted location to electronically retrieve the stored data but suppress display thereof; and following detection of the user's presence at the predicted location, displaying the retrieved data on the device at the predicted location.

In various embodiments, the retrieved data is displayed only following authentication of the user at the device at the predicted location. Authentication may, for example, comprise communication of data to an authentication server, and may satisfy a security policy specific to the retrieved data. In some embodiments, the method further comprises the step of causing the device at the predicted location to launch an application to display the retrieved data.

The method may also include, following detection of the user's presence at the predicted location, predicting (i) a second future location of the user different from the predicted location and (ii) stored data required by the user at the second future location; causing a device at the second predicted location to electronically retrieve the stored data but suppress display thereof; and following detection of the user's presence at the second predicted location, displaying the retrieved data on the device at the second future location.

In some embodiments, the stored data is determined by the predicted location and an individual currently at the predicted location. Information about the user may comprise or consist of information relevant to a security policy, e.g., a clinical role of the user and a list of patients assigned to the user.

In another aspect, the invention pertains to a system for anticipatory provisioning of resources for a mobile user in an institutional space. In various embodiments, the system comprises a plurality of devices at different locations in the institutional space; a location server in operative communication with the devices via a network and including (A) computer storage defining a user location database that itself includes records for a plurality of users, each of the records including data indicative of a current location of the user and information about the user, and (B) a prediction module for predicting, based on a location and the information about the user in the corresponding database record, (i) a future location of the user and (ii) stored data required by the user at the future location; and a desktop server in operative communication with the devices and the location server via the network, the desktop server being configured to cause a device at the predicted location to electronically retrieve the stored data but suppress display thereof and, following detection of the user's presence at the predicted location, to display the retrieved data.

The system may also include an authentication server for receiving user log-on credentials and thereupon signaling the device at the predicted location display the retrieved data. The user log-on credentials may satisfy a security policy specific to the retrieved data. In various embodiments, the stored data is determined by the predicted location and an individual currently at the predicted location. Information about the user may comprise or consist of information relevant to a security policy, e.g., a clinical role of the user and a list of patients assigned to the user.

In still another aspect, the invention relates to a system for managing location-based events in an institutional space. In various embodiments, the system comprises a plurality of tracking sensors at different locations in the institutional space, each of the tracking sensors being configured to detect a proximate presence of an individual or a device and to produce signals indicative thereof; a plurality of application host devices distributed within the institutional space, each of the application host devices running an application; and a location server in operative communication with the tracking sensors and the application host devices via a network. The location server further includes computer storage defining (i) a user location database that stores records for a plurality of users, each of the records including a current location of the user based on signals from the tracking sensors; (ii) a device location database that stores records for a plurality of devices, each of the records including a current location of the device; and (iii) a subscription database that stores records for a plurality of applications each running on a different device; each of the records specify an application and one or more location events to which the application has subscribed. The location server is configured to receive signals from the tracking sensors, interpret the received signals as events, and notify applications upon occurrence of events to which they subscribe.

The system may further comprise an authentication server including a stored security policy accessible thereto, where the security policy specifies authentication events required to access at least some of the applications, and the authentication server is in communication with the application host devices to control access to applications running thereon. At least some of the required authentication events may be based on a location of the associated application host device. The security policy may specify actions to be taken in response to walk-up events consisting of an individual's entry within a monitored geospatial zone and walk-away events consisting of an individual's departure from a monitored geospatial zone. For example, the authentication server may be configured to receive notifications of the walk-away events from applications subscribing thereto and responsively take action based on the security policy. That action may be, for example, closing or prevent access to the applications. In various embodiments, the security policy relaxes authentication requirements based on the location of the associated application host device.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and may exist in various combinations and permutations. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, routines, steps, or characteristics may be combined in any suitable manner in one or more examples of the technology. As used herein, the terms "approximately" and "substantially" mean±10%, and in some embodiments, ±5%.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

Figure 1:
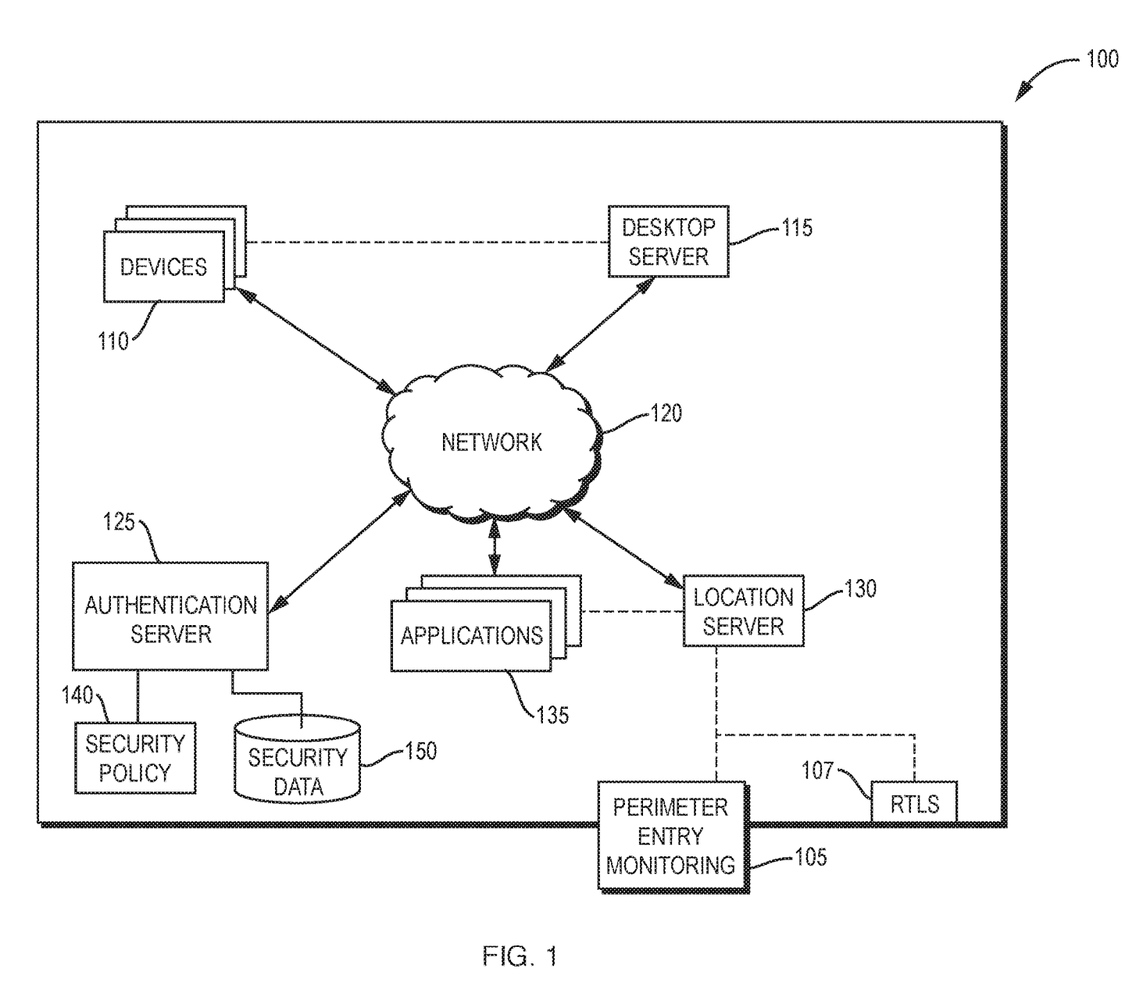
FIG. 1 schematically illustrates an institutional space including devices and servers in accordance with embodiments of the invention.

Refer first to FIG. 1, which illustrates a generalized environment in which embodiments of the invention may be deployed. The environment is an institutional space 100, such as a hospital, which may include multiple buildings each including perimeter-entry monitors 105. These may, for example, be card readers that detect and log user entry into the institution and/or restrict entry to secure areas to authorized personnel. An RTLS system 107 monitors the changing locations of users with the space 100 (e.g., via wireless detection of tags worn by users and/or affixed to devices they carry, by face recognition, or any other suitable means). A typically large number of devices 110, which may be movable within the space 100, are available for mobile users (i.e., clinicians who roam from place to place within the space 100) as they discharge their responsibilities. These devices 110, which include workstations, thick or thin client devices, kiosks, and network-connected medical devices are herein referred to collectively as "nodes." In general, a node is able to access, via a network, one or more data stores that include information (e.g., EMR) of interest to clinicians.

A desktop server 115 generates "virtual desktops" for users that are displayed on one of the devices 110 when the user logs in at that device. Particularly in secure environments or where sensitive data is accessed, many applications are not launched locally at the device 110 but are provided through a portal or "desktop agent," such as XENDESKTOP (supplied by Citrix Corp.) or the like, running on the device 110. The portal is in communication with desktop server 115 via a network 120. In a virtual-desktop environment, applications run within a hosted session generated on a secure, "locked-down" desktop server 115, which can create and maintain many simultaneous sessions at different devices 110. See, e.g., U.S. Pat. Nos. 8,866,701 and 9,009,219, the entire disclosures of which are hereby incorporated by reference.

Log-on may be handled by a separate authentication server 125, which authenticates users based on their credentials in accordance with an institutional security policy 140 stored on or available to authentication server 125. That policy may require different tiers of authentication depending on the data to which the user seeks access; for example, a simple password log-in may be sufficient for access to routine applications, while a "strong" modality such as a biometric (e.g., fingerprint or vein) scan may be required for access to secure data. A location server 130 maintains awareness of the locations of users within the space based on indicators such as the device on which the user's current session is active or, if the device location is unknown or no session is active, based on perimeter accesses and RTLS 207. RTLS reference points, which can be either transmitters or receivers, are spaced throughout a facility to detect the presence of identified tags.

A plurality of applications, representatively illustrated at 135 and hosted on nodes, "subscribes" to events monitored by location server 130. As described in greater detail below, this means that applications register with location server 130 to receive notification of particular events. These events may be represented an any level of granularity selected by the system designer, and the available choices may depend on the capabilities of location server 130. For example, an application 135 that retrieves and displays EMR data may, upon launch, subscribe to receive notifications of all walk-away events relating to the device on which it is running. (Walk-away and walk-up events may be detected using a camera or the time-varying signal strength from a mobile device; see, e.g., U.S. Ser. No. 13/920,613 and Ser. No. 14/945,609, and U.S. Pat. No. 8,538,072, the entire disclosures of which are hereby incorporated by reference.) In this case, location server 130 is responsible for gathering and filtering all walk-away events and notifying only those applications to which a particular event is relevant; it must also detect (or be informed by the application 135 of) the device on which the subscribing application 135 is running. In this connection, it should be stressed that applications 130 may be hosted locally, on a workstation or user device, or remotely on an application server. So long as the application can communicate with location server 130 via network 120, the manner in which the application is hosted does not matter. If the network protocol (e.g., ETHERNET) over which the application 135 and location server 130 communicate requires packets to identify the source device, location server 130 can readily infer the relevant device from the initial subscription request.

The security policy 140 may have a locational component, and as a result, authentication server 125 may subscribe to events relevant to the policy 140 and, in some embodiments, stores in a database 150 data relating to currently active applications and resources to which it has granted access. The stored data can specify a user, device, location, proximity, and/or previous authentication events. For example, authentication requirements for a user to access a resource may differ depending on the user's current location, since presence in a secure area means that the user has already presented some form of credential (such as an access card), which may serve as one factor of a two-factor authentication requirement. Although authentication server 125 might not subscribe to every location-related event that could prove relevant to an authentication decision, it can request relevant information from location server 130 when the user attempts to authenticate—e.g., inquiring whether the user is currently within an access-controlled space if this is not evident from the request-originating user device. On the other hand, authentication server 125 may subscribe to all walk-away events, or all walk-away events pertaining to secure resources for which authentication is required. Once a walk-away event is detected and notification thereof received by authentication server 125, the server may terminate the user's session with the secure resource or cause temporary launch a privacy screen-saver on the device from which the user walked away. If a walk-up event involving the same user and device is detected within a short time after the detected walk-away event, the privacy screen may be automatically removed and the user once again accorded access to the secure resource. In one representative workflow, once the user has first authenticated and obtained access to the secure resource, authentication server 125 subscribes to all location events involving the user and the device. It therefore receives notification of the walk-away event, since this involves both the user and the device, and causes the accessing device to launch a privacy screen-saver. When the user returns, location server 130 may report both a generic walk-up event (which itself would be insufficient) as well as proximity detection of a mobile device associated with the user. If this information, in combination with a short time between walk-away and walk-up events, is sufficient to satisfy security policy 140, authentication server 125 may cause the privacy screen to be removed. As a result, the user automatically receives immediately renewed access to the secure resource without any action or new authentication.

As used herein, the term "application" means any running process on a computational device, and in a medical setting can include healthcare information (e.g., EMR) and workflow (e.g., CPOE) systems as well as conventional software such as word processors, spreadsheets, and browsers. Applications may be configured to operate freely as long as non-sensitive information is accessed. When the user operates an application to request secure data or access to a secure resource, the application communicates with authentication server 125 and permits access only upon successful authentication in accordance with the applicable security policy. Of course, events need not relate to security; at a more general level, applications subscribe to events that are relevant to tasks or workflows they support (either autonomously or in concert with other applications). Moreover, monitored individuals are not limited to application users— for example, patients as well as their caregivers and hospital staff may be tracked by location server 130. A CPOE system, for example, may subscribe to events involving all currently resident patients (tracked by bracelets or wireless tags encoding patient IDs) for whom prescriptions have been written. When a clinician dispenses a drug to a patient, the CPOE system may ensure that the patient is actually co-located with the clinician. For example, before actually administering medication to a patient, a clinician may scan a barcode accompanying the medication, and which encodes the patient ID; the CPOE responds to the read barcode by consulting a database of patients, their IDs, and their current locations, which are updated each time location server 130 registers a change in patient location; that is, the CPOE system subscribes to location events involving all patients in the database (which itself changes dynamically as prescriptions for new patients are written and patients are discharged). The CPOE also determines the location of the administering clinician (who has previously logged into the CPOE), who, for example, may be wearing a tag or carrying a mobile device tracked by RTLS 107. If the administering clinician is not co-located with (e.g., at least in the same room as) the proper patient, the clinician may be alerted by, for example, a visual and/or audible signal emitted by the barcode reader to avoid improper drug administration.

As shown in FIG. 1, the network 120 supports communication among devices 110, applications 135, and servers 115, 125, 130. The term "network" is herein used broadly to connote wired or wireless networks of computers or telecommunications devices (such as wired or wireless telephones, tablets, etc.). For example, a computer network may be a local area network (LAN) or a wide area network (WAN). When used in a LAN networking environment, computers may be connected to the LAN through a network interface or adapter. When used in a WAN networking environment, computers typically include a modem or other communication mechanism. Modems may be internal or external, and may be connected to the system bus via the user-input interface, or other appropriate mechanism. Networked computers may be connected over the Internet, an Intranet, Extranet, Ethernet, or any other system that provides communications. Some suitable communications protocols include TCP/IP, UDP, or OSI, for example. For wireless communications, communications protocols may include IEEE 802.11x ("Wi-Fi"), Bluetooth, Zigbee, IrDa, near-field communication (NFC), or other suitable protocol. Furthermore, components of the system may communicate through a combination of wired or wireless paths, and communication may involve both computer and telecommunications networks. For example, a user may establish communication with a server using a "smart phone" via a cellular carrier's network (e.g., authenticating herself to the server by voice recognition over a voice channel); alternatively, she may use the same smart phone to authenticate to the same server via the Internet, using TCP/IP over the carrier's switch network or via Wi-Fi and a computer network connected to the Internet.

It should also be understood that while the servers 115, 125, and 130 are shown as physically separate devices within the institutional space 100, this is for illustrative purposes only. Multiple servers may in fact reside on the same computer, and may be "virtualized." Moreover, even separate machines need not reside in the institution's on-site data center; many facilities, for example, contract with a third party for authentication services delivered "in the cloud," i.e., remotely over the Internet or the public telecommunications in a manner that is indistinguishable, to users, from a wholly local implementation. Accordingly, references herein to "servers" have no topological or device-level connotation; any functionally satisfactory deployment scheme, whether on a single or multiple machines wherever located, are within the scope of the present invention.

Figure 2:
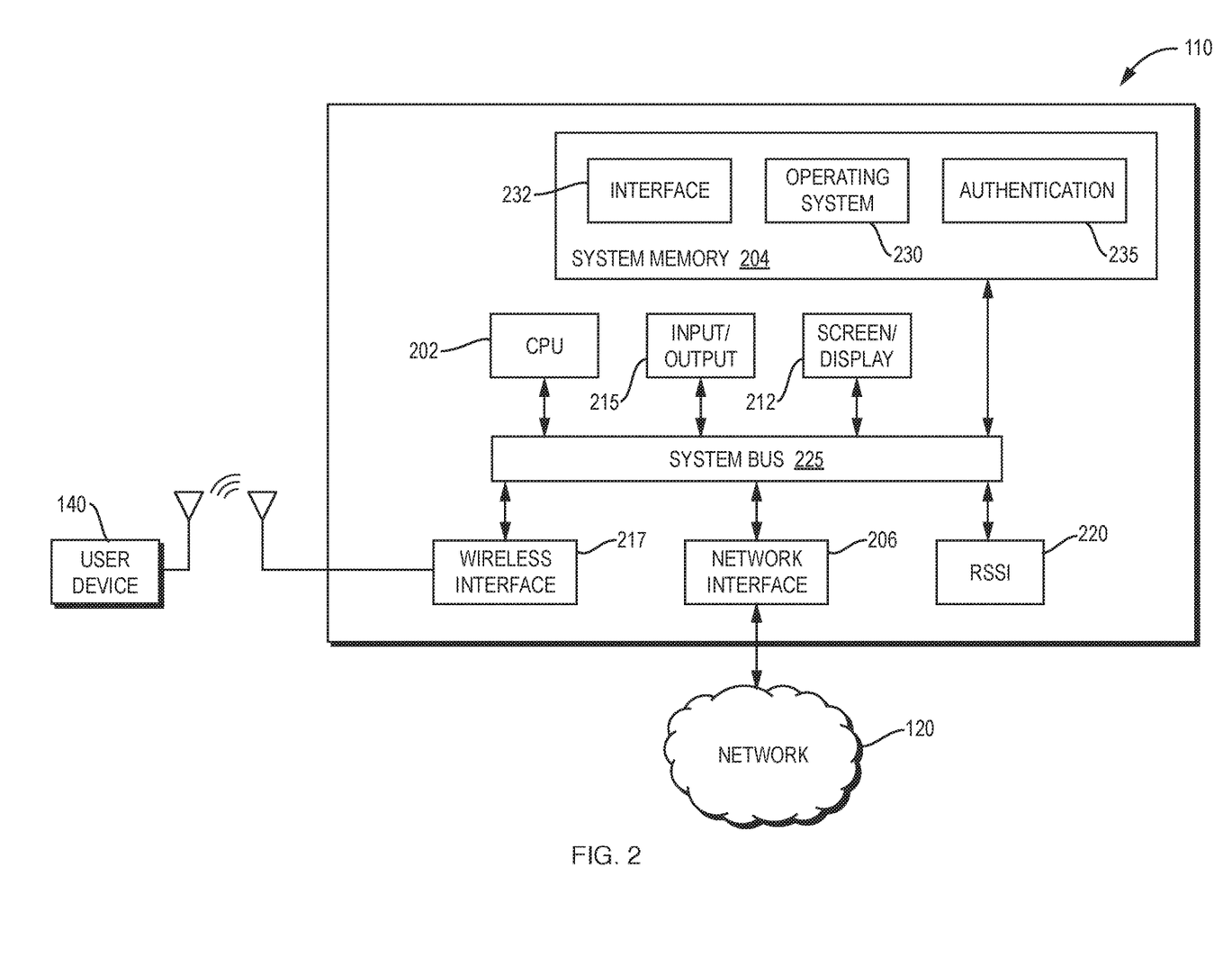
FIG. 2 schematically illustrates a node in accordance with embodiments of the invention.

FIG. 2 illustrates a representative node 110, which may be a workstation (e.g., a general-purpose personal computer running suitable software), a fat or thin client device, a kiosk, a network-connected medical device, or any other device with which clinicians and other users interact, and which may be moved from time to time within an institutional setting. Node 110 typically includes a processor 202 (e.g., a CPU microprocessor) and associated system memory 204, a network interface 206 (for connection to the institutional network 120 and/or the Internet), and, usually, one or more non-volatile digital storage elements (such as a hard disk, CD, DVD, USB memory key, etc.) and associated drives. Further, workstation 110 includes user input/output devices such as a display screen 212 and conventional tactile input devices 215 such as keyboard and mouse or touch pad. A wireless interface 217, which may be separate from or implemented within network interface 206, facilitates wireless communication with user mobile devices. In some embodiments, workstation 110 includes a received signal-strength indication (RSSI) circuit 220, which, again, may be implemented within or separate from the wireless interface 217. The various components communicate with each other via one or more buses 225.

In use, processor 202 executes one or more computer programs (conceptually illustrated as program modules) stored in system memory 204. An operating system 230 (such as, e.g., MICROSOFT WINDOWS, UNIX, LINUX, iOS, or ANDROID) provides low-level system functions, such as file management, resource allocation, and routing of messages from and to hardware devices (such as I/O device(s) 215) and one or more higher-level user applications (such as EMR applications, office programs, a web browser, etc.) An interface 232 generates screen displays and receives user input via the input devices, e.g., by the user's typing on the keyboard, moving the mouse, or clicking with the mouse on a displayed control element. In some implementations, node 110 includes an authentication agent 235 that allows a user to obtain access to restricted data consistent with his privilege level and the security policies of the institution. Authentication agents are known in the art and described, for example, in U.S. Ser. No. 11/294,354, filed Dec. 5, 2005, the entire disclosure of which is hereby incorporated by reference, and may communicate with a remote authentication server that securely stores user credentials. A desktop agent module 240 facilitates use of and interaction with remotely hosted applications via screen display 212, and also allows the user to modify settings on the application host server. For example, the user may specify or modify preferences, such as a set of default applications to be launched when a virtual desktop for the user is created.

Figure 3:
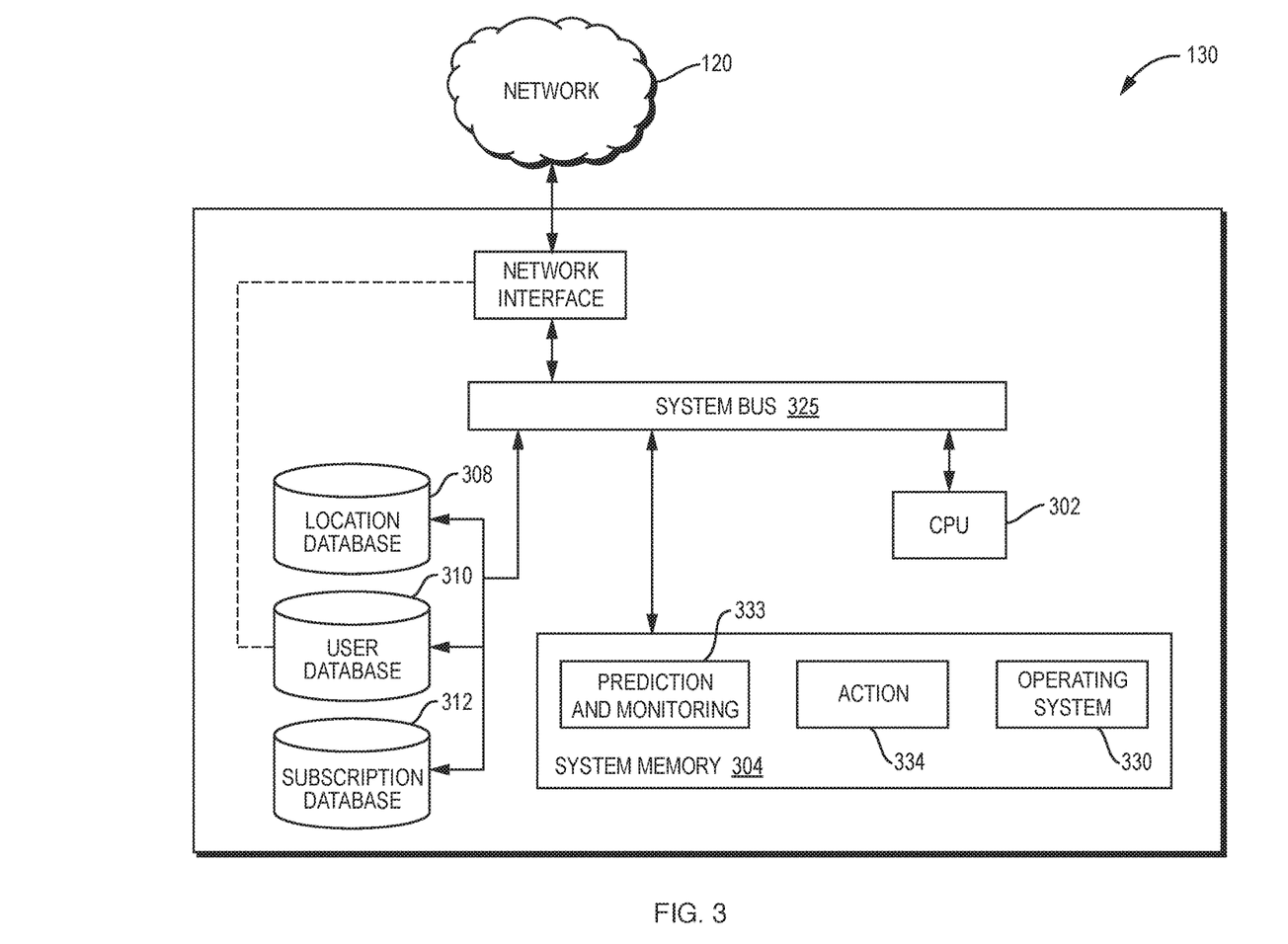
FIG. 3 schematically illustrates a location server in accordance with embodiments of the invention.

FIG. 3 illustrates a location server 130 that also typically includes a processor 302 (e.g., a CPU) and associated system memory 304, a network interface 306, a system bus 325, and one or more non-volatile digital storage elements including a location database 308, a user database 310, and a subscription database 312. The databases 308, 310, 312 may be stored locally as separate files or disk partitions, or may be stored remotely and accessed via network interface 306. Location database 308 stores records each specifying a node and its most recently determined physical location, and may also indicate its distance from other nodes. User database 310 stores records each specifying a user, location information for the user as described in greater detail below, a provisioning policy for the user, and, in some cases, a user privilege level. Subscription database 312 stores records each specifying an application and events or event categories to which the application has subscribed. Applications may subscribe and unsubscribe dynamically to different events depending on context; for example, as described earlier, when a secure application is launched (or when a general-purpose application requests access to secure data), it may either autonomously subscribe to security-related events or, instead, may be automatically subscribed by authentication server 125 upon initial user authentication. These subscriptions may be removed once the user exits the application or logs off. Authentication server 125 may also subscribe in the manner of an application each time an authentication event occurs and the applicable security policy has a locational component.

This multi-database arrangement provides flexibility in separating the task of keeping track of nodes and the task of keeping track of user activity and preferences the former involving ongoing location awareness of nodes that may move and the latter involving ongoing awareness of current user activity and location. It also separates detection and logging of events from their application-level consequences. It should be stressed, however, that any number of databases, including a single database, may be used. Physical device locations may be obtained in any suitable fashion, e.g., entered once for fixed devices or reported by the devices or by others as devices are moved.

System memory 304 includes stored instructions defining an operating system 330. In addition, memory 304 stores a prediction and monitoring application 333 that, in various embodiments, predicts the next location of a user in response to a location-based triggering event (e.g., the detected departure of the user from a node), and an action module 334 that causes an action to be taken based on the triggering event. More generally, server 130 (as well as servers 125 and 115, which are conventional) may be implemented on any suitable computing platform including a processing unit, a system memory, and a system bus that couples various system components including the system memory to the processing unit. During operation, the system memory contains the instructions implementing the functionality described herein. Computers typically include a variety of computer-readable media that can form part of the system memory and be read by the processing unit. By way of example, and not limitation, the system memory may include computer storage media in the form of volatile and/or nonvolatile memory such as read only memory (ROM) and random access memory (RAM). A basic input/output system (BIOS), containing the basic routines that help to transfer information between elements, such as during start-up, is typically stored in ROM. RAM typically contains data and/or program modules that are immediately accessible to and/or presently being operated on by processing unit. The data or program modules may include an operating system, application programs, other program modules, and program data. The operating system may be or include a variety of operating systems such as Microsoft WINDOWS operating system, the Unix operating system, the LINUX operating system, the Xenix operating system, the IBM AIX operating system, the Hewlett Packard UX operating system, the MACINTOSH operating system, the APACHE operating system, an OPENSTEP operating system or another operating system of platform.

Anticipatory provisioning may involve maintaining a consistent desktop session from device to device or optimistic pre-caching of data at predicted locations. Desktop sessions are maintained by desktop server 115 (see FIG. 1), which may run one or more thin-client computing or remote display presentation applications. In one embodiment, server 115 executes as an application any portion of the CITRIX ACCESS SUITE by Citrix Systems, Inc., such as the METAFRAME or CITRIX PRESENTATION SERVER products, or applications such as CITRIX XENAPP, CITRIX XENDESKTOP, CITRIX ACCESS GATEWAY, and/or any of the MICROSOFT WINDOWS Terminal Services from Microsoft Corporation. As is conventional, desktop server 115 may maintain a default list of applications for each user (which list may be modified, either directly by the user or based on user activity) and session data. The session data enables a current session state to be fully replicated— i.e., each application as well as retrieved data are stored, either directly or (more commonly) as pointers, so that the user may continue a current session on a new virtual desktop launched, using the session data, on a different node. When the virtual desktop is created from the "golden image" (i.e., a master template), the current or default record data is used to deliver applications and retrieve data in accordance with the user's record in database 310.

Thus, a "virtual desktop," as that term is used herein, broadly refers to a particular suite of applications launched by or otherwise delivered to a user, and data either typically or currently accessed by the user. In some circumstances, the virtual desktop represents the state of the user's current or most recent session on a node, including applications launched and user-requested data. In other circumstances, the virtual desktop is a representative session tailored to the particular user, either based on a registration sequence in which the user specifies applications to be launched at startup, or based on monitoring of user activity. It should also be stressed that a virtual desktop can be a browser-based session connected to a hosted webserver, which may deliver either applications or a web session via the browser. The web session may be a portal for other applications or even a web-delivered desktop. Accordingly, virtual desktops as understood herein do not require specialized infrastructure for delivery and use.

The current state of a user's hosted session is maintained in user database 310 and is easily updated, for example, by the desktop agent 240 resident on the user's current node 110 in response to a location-based triggering event. Desktop agent 240 monitors applications launched locally and remotely via the node 110, and adds identifiers for these applications to the user's record in user database 310. In addition, desktop agent 240 agent monitors data retrieved by the user (typically, though not necessarily, via one of the applications) and adds identifiers for these as well. For example, retrieved data may include documents opened in a word processor, patient records accessed via an EMR system, lab reports, real-time patient data obtained remotely from a medical device, etc. In some circumstances, the current data may be deleted and the default options reinstated—e.g., after a sufficiently long period has elapsed since session log-off that the prior session is unlikely to be relevant, or if the user has entered a different institutional facility. If the user has logged off from a session, or the session has timed out (i.e., has been deleted due to persistent inactivity), desktop server 115 will provision the user's default applications. If the user has not logged off, or has instructed desktop server 115 to save the current session, that session will be recreated for the user at the appropriate time—and just what time is appropriate may depend on various factors.

Alternatively, anticipatory provisioning may take place outside the scope of existing user sessions, e.g., by optimistic launching of applications with which the user has not yet interacted or, if the application is already running, optimistic data caching. Thus, desktop server 115 (or a separate application server) may be configured to host applications remotely and make them available on target devices and/or cause applications to be launched locally on a target device. Desktop server 115 may, for example, be programmed to subscribe to predicted location events involving particular individuals (whose routines make them good candidates for optimistic launching, for example). With reference to FIGS. 1 and 3, if prediction and monitoring application 333 predicts that a clinician is headed for particular location and is likely to require a certain application when he gets there, location server 130 may signal desktop server 115 to launch the application on a device at the predicted location but with disabled visibility; the application becomes visible when the user's presence is detected. For example, suppose a surgeon has patients in a hospital's intensive-care unit. When the surgeon reaches her first patient, her location is registered by location server 130. Prediction and monitoring module 333, after consulting databases 308, 310, determines that two other patients of the surgeon are located in the same intensive-care unit, and as a result, the surgeon is likely to soon visit both. Location server 130 signals desktop server 115 to bring up the EMR of the closest of the two other patients on a device in the patient's room, but disabling user input and visibility so that the data is ready but not active. When the surgeon actually enters the second patient's room, approaches the device, and gestures (e.g., waving a registered mobile device) or touches a proximity reader, she is recognized by the local hosting device, which—either autonomously or following communication with authentication server 125 so as to satisfy security policy 140 unlocks the input capability and removes the privacy screen, making the data visible and input-capable. The surgeon having departed from the previous patient's room, desktop server 115 may tear down the EMR application in that patient's room immediately or keep it alive, with the privacy screen restored, for a short time in case the surgeon returns. The foregoing prediction and opportunistic caching steps are further repeated and data is cached at a device co-located with the third of the surgeon's patients in the intensive-care unit. If, on the other hand, the surgeon does not arrive at the second patient's room after a predetermined period of time (e.g., a multiple of the estimated time it should take the surgeon to walk there) elapses following her detected departure from the first patient's room, the EMR application may be torn down.

The timing and mode of provisioning reflect a trade-off between use of system resources and the immediacy and scope of a user's need. A virtual desktop presumes an existing user desktop session and the need for access to all applications active in the session; the virtual session may be delivered on a node as soon as the user has logged on and authenticated himself at the node, or may not even be assembled until the user logs on. To reduce resource utilization, a user's default applications are not launched, or a current session is not regenerated at desktop server 115, until the user actually logs in. This minimal approach reflects common conventional practice. The latency experienced by a user may be reduced by instantiating a new (default) session or maintaining a current session on desktop server 115, so that when the user logs in at a new node, the virtual desktop has already been created and can be delivered there. For example, a default virtual desktop may be created at desktop server 115 when a user's presence is initially detected at the facility or, in some implementations, in a particular location (e.g., department). The latency experienced by the user is minimized when the virtual desktop is delivered to a predicted location and, when it becomes active, is hidden from view until the user logs in.

The ability to avoid virtualizing and regenerating a desktop session obviously reduces resource utilization, so anticipatory caching of application data—particularly if an instance of the relevant application is already running on the target device—is a far more lightweight option than desktop provisioning. In some instances, applications may be configured to give the user the option to quit or suspend the desktop session and specify a destination device or location, and also to select whether to provision the entire desktop or just a current application. If the destination device is associated with a particular individual in database 310—e.g., with a patient because the device is located in the patient's room—desktop server 115 may cause the launched instance of the application to retrieve information associated with that patient.

Following a location-based triggering event, the user's record in user database 310 is updated, and is updated again the next time the user is detected at a monitored location. As noted above, the user's current location may be based on indicators such as the device on which the user's current session is active or, if the device location is unknown or no session is active, based on perimeter accesses and RTLS. To support the operation of prediction and monitoring module 333, user database 310 may maintain a history of sequentially detected user locations, e.g., over the course of a day or longer period.

A location-based triggering event can be any detectable event suggesting a user change of location. For example, when a user logs off a current session, or if a walk-away event is detected at the user's current node, a triggering event may be recorded by module 333; more specifically, in the illustrated embodiment, the current node reports the log-off or walk-away event to location server 300, and module 333 both updates the user record in database 310 to reflect an unknown current user location and takes action based on the provisioning policy in the user record. Other location-based detection events can include log-in at a device other than that listed as the user's current device in user database 310 (indicating that the user has departed from the listed device without logging off or having the departure detected), or presence detection at a location different from the location of the device listed as the user's current device in user database 310. More generally, any event associating the user with a current location e.g., passing through perimeter security, having an access card or user-associated mobile device detected by a reader, etc.—can be detected and reported to module 333. Depending on the provisioning policy associated with the user, such events may only have significance (i.e., cause an action to take place) if a current user device and/or desktop server 115 reports the user as having logged on via authentication server 125. In this way, resources are not committed for users who have not yet begun sessions and/or authenticated themselves. For some users, however, mere detection may cause a virtual desktop to be created. For example, for some personnel (e.g., surgeons and supervisory personnel), the virtual desktop may be created as soon as the individual's presence within a facility is detected, e.g., by perimeter entry system 105, or when s/he is detected (e.g., by a beacon or RTLS 107) near a particular location within the facility. These location criteria and associated actions are stored in the provisioning policy field of the user's record in database 310, e.g., as a privilege level.

With reference to FIGS. 1-3, in a representative operational sequence, location server 300 registers a location-based triggering event involving a user. In response, module 333 retrieves from user database 310 the provisioning policy associated with the user. Module 333 may signal desktop server 115 to save the current session state of the user; for example, module 333 may retrieve from database 310 the identifier of the device at which the triggering event was detected and instruct desktop server 115 to save the current session state at this device (and, in some cases, also to terminate the session to avoid unwanted visibility of sensitive data on the device display) and/or to maintain the user's virtual desktop so that it may be accessed directly from a different device (following user authentication thereon).

Module 333 may predict the next location or device where the user is expected to appear. In some embodiments, module 333 uses a simple rule base to predict the node that a user is most likely to use next. Such an approach is feasible where user activity tends to follow established patterns. For example, if module 333 detects that a surgeon has just departed a hospital's imaging department after viewing a patient's CAT scan, it may query a hospital information server for the current location and status of the patient whose scan was being viewed. If the patient is scheduled for surgery, module 333 may query location database 308 to determine the device closest to the surgical suite where the patient is expected to soon arrive, and instruct desktop server 115 to deliver a virtual desktop to this device and recreate thereon the saved user session.

If actions beyond instructing the desktop server 115 to deliver a virtual desktop are contemplated, they may be executed by the dedicated action module 334. For example, in response to a triggering event, action module 334 may cause commands to be sent via network interface 206 to set the closest printer associated with the target device where the virtual desktop will be delivered; bridge USB devices associated with the target device so they can be accessible by the hosted session when the user arrives at the target device; retrieve and display a census of the patients on the floor that the provider needs to see; cause additional applications outside the virtual desktop to be launched at the target device or at a neighboring or connected device; and connecting and enabling dictation at the target location.

Module 333 may also base a location prediction on past activity and/or correlations between application use and subsequent activities, using, for example, conventional unsupervised learning or neural-net techniques. In these embodiments, a location history maintained for each user in database 310 is used to update the predictive model. For example, the user's daily monitored movements may be used to update the model at the end of a day.

The timing of creation and delivery may depend on the identity of the user and the degree of confidence in a prediction. In some embodiments, virtual desktops are assembled and, in some cases, delivered to a node in advance for users who, for example, frequently move among nodes; such users would otherwise repeatedly suffer start-up delays as virtual desktops are prepared, and the commitment of additional computational resources to prepare the desktop in advance is merited for such users. A user's priority determining whether a virtual desktop is prepared in advance may depend on a privilege level associated with the user in database 310. For high-priority users, the virtual desktop may be prepared as soon as the user's entry into the facility has been registered, and it may be delivered to the node that the user is likely to access first (e.g., based on past history). After these high-priority users have logged in, a location-based triggering event indicative of departure from a node may be sufficient to cause delivery of a virtual desktop to a predicted next node; while for lower-priority users, a second location-based triggering event indicative of arrival at a node is necessary to cause delivery of the virtual desktop to that node.

In some embodiments, the virtual desktop is not created (or delivered to the predicted next node) unless a sufficiently high confidence level is registered (or unless the user's privilege level is sufficiently high). The confidence level may be based on various factors—most simply, the user's history of movement patterns among nodes. However, the desktop server may consider corroborating factors tending to reinforce the prediction (in a manner analogous to optimistic caching). For example, if, having walked away from node A, past activity patterns (of the particular user or generally among users) suggest the user will next log on at node B, the confidence level is increased if RTLS detects the user in proximity to node B or predicts a trajectory encompassing node B. Setting up the virtual desktop at this point of prediction rests on a relatively high confidence level that the operations will not be wasted, and occurs sufficiently in advance of the user's actual arrival at node B to avoid set-up delay when the user logs on. Conversely, delivery may be suspended if the predicted node is currently in use by someone else, or delivery may be shifted to a nearby node (particularly if there are no other nodes in the vicinity). If the user passes the predicted node without stopping, the virtual desktop may be revoked from the predicted node, at which point the desktop server may predict a new destination for the user. In this context, revocation generally means that the provisionally established connection between the virtual desktop and the predicted device is broken.

Preferably, it is the user's physical destination, rather than the identifier of a particular device that can be moved, which is predicted. Records in location database 308 associate a predicted destination with the device currently at that location.

Any suitable programming language may be used to implement without undue experimentation the functions described above, including those of desktop agent 240 and prediction and monitoring module 333, with processing responsibility allocated between node 110 and servers 115, 130 as desired by the system designer. Illustratively, the programming language used may include assembly language, Ada, APL, Basic, C, C++, C*, COBOL, dBase, Forth, FORTRAN, Java, Modula-2, Pascal, Prolog, Python, REXX, and/or JavaScript, for example. Further, it is not necessary that a single type of instruction or programming language be utilized in conjunction with the operation of the system and method of the invention. Rather, any number of different programming languages may be utilized as is necessary or desirable.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A method of anticipatory provisioning of resources for a mobile user in an institutional space, the method comprising the steps of:
   providing a database storing records for a plurality of users, each of the records specifying information about one of the users;
   detecting, at a first device at a first location, access to a secure resource by a previously authenticated user having a record in the database;
   detecting a walk-away event at the first device and, in response, causing a privacy screen to be launched at the first device;
   based on the first location and the information about the user in the corresponding database record, predicting (i) a future location of the user and (ii) stored data required by the user at the future location;
   causing a second device at the predicted location to electronically retrieve the stored data but suppress display thereof with a privacy screen thereover;
   detecting a walk-up event of the user to the second device, the walk-up event indicating the user's presence at the predicted location;
   following detection of the walk-up event at the second device, displaying the retrieved data on the second device at the predicted location by removing the privacy screen.

2. The method of claim 1, wherein the retrieved data is displayed on the second device without re-authenticating the user at the second device at the predicted location.

3. The method of claim 1, wherein authentication comprises communication of data to an authentication server.

4. The method of claim 3, wherein authentication satisfies a security policy specific to the retrieved data.

5. The method of claim 1, further comprising the step of causing the device at the predicted location to launch an application to display the retrieved data.

6. The method of claim 1, further comprising, following detection of the user's presence at the predicted location:
   predicting (i) a second future location of the user different from the predicted location and (ii) stored data required by the user at the second future location;
   causing a device at the second predicted location to electronically retrieve the stored data but suppress display thereof; and
   following detection of the user's presence at the second predicted location, displaying the retrieved data on the device at the second future location.

7. The method of claim 1, wherein the stored data is determined by the predicted location and an individual currently at the predicted location.

8. The method of claim 7, wherein the individual is not the previously authenticated user.

9. The method of claim 7, wherein the individual is a patient of the previously authenticated user.

10. The method of claim 1, wherein information about the user comprises information relevant to a security policy.

11. The method of claim 10, wherein the information comprises a clinical role of the user and a list of patients assigned to the user.

12. The method of claim 1, wherein the user is previously authenticated at a location within the institutional space different from the first location.

13. The method of claim 1, wherein detecting the walk-up event of the user to the second device comprises detecting presence of a mobile device associated with the user proximate the second device.

14. The method of claim 1, wherein the user accesses the secure resource at the first device during a first session, and further comprising the step of keeping the first session active for a period of time following detection of the walk-away event at the first device.

15. The method of claim 14, further comprising the step of removing the privacy screen at the first device following detection of a walk-up event of the user to the first device during the period of time.

16. The method of claim 14, further comprising the step of removing the first session after the period of time if no walk-up event of the user to the first device is detected during the period of time.

17. The method of claim 14, further comprising the step of removing the first session upon detecting the walk-up event of the user to the second device.

18. A system for anticipatory provisioning of resources for a mobile user in an institutional space, the system comprising:
   a plurality of devices at different locations in the institutional space;
   a location server in operative communication with the devices via a network and including:
      computer storage defining a user location database that itself includes records for a plurality of users, each of the records including data indicative of a current location of the user and information about the user; and a processor for executing a prediction and monitoring module and an action module, wherein the prediction and monitoring module is configured to:
A) detect, at a first device at a first location, (i) access to a secure resource by the user and (ii) a subsequent walk-away event of the user the first device, and
B) predict, based on a location and the information about the user in the corresponding database record, (i) a future location of the user and (ii) stored data required by the user at the future location; and the action module is configured to cause, in response to the detected walk-away event, a privacy screen to be launched at the first device; and a desktop server in operative communication with the devices and the location server via the network, the desktop server being configured to cause a second device at the predicted location to electronically retrieve the stored data but suppress display thereof with a privacy screen thereover and, following detection of a walk-up event of the user to the second device, the walk-up event indicating the user's presence at the predicted location, to display the retrieved data at the second device by removing the privacy screen.

19. The system of claim 18, further comprising an authentication server for receiving user log-on credentials and thereupon signaling the second device at the predicted location to display the retrieved data.

20. The system of claim 19, wherein the user log-on credentials satisfy a security policy specific to the retrieved data.

21. The system of claim 18, wherein the stored data is determined by the predicted location and an individual currently at the predicted location.

22. The system of claim 18, wherein information about the user comprises information relevant to a security policy.

23. The system of claim 22, wherein the information comprises a clinical role of the user and a list of patients assigned to the user.

24. A system for managing location-based events in an institutional space, the system comprising:
a plurality of tracking sensors at different locations in the institutional space, each of the tracking sensors being configured to detect a proximate presence of an individual or a device and to produce signals indicative thereof;
a plurality of application host devices distributed within the institutional space, each of the application host devices running an application; and
a location server in operative communication with the tracking sensors and the application host devices via a network, the location server further including computer storage defining:
(i) a user location database that stores records for a plurality of users, each of the records including a current detected location of the user based on signals from the tracking sensors;
(ii) a device location database that stores records for a plurality of devices, each of the records including a current location of the device; and
(iii) a subscription database that stores records for a plurality of applications each running on a different device, each of the records specifying an application and one or more location events to which the application has subscribed,
wherein the location server is configured to receive signals from the tracking sensors, interpret the received signals as events, and notify applications upon occurrence of events to which they subscribe.

25. The system of claim 24, further comprising an authentication server including a stored security policy accessible thereto, the security policy specifying authentication events required to access at least some of the applications, wherein the authentication server is in communication with the application host devices to control access to applications running thereon.

26. The system of claim 25, wherein at least some of the required authentication events are based on a location of the associated application host device.

27. The system of claim 26, wherein the security policy relaxes authentication requirements based on the location of the associated application host device.

28. The system of claim 25, wherein the security policy specifies actions to be taken in response to walk-up events consisting of an individual's entry within a monitored geospatial zone and walk-away events consisting of an individual's departure from a monitored geospatial zone.

29. The system of claim 28, wherein the authentication server is configured to receive notifications of the walk-away events from applications subscribing thereto and responsively take action based on the security policy.

30. The system of claim 29, wherein the action is closing or prevent access to the applications.

* * * * *